US 9,921,588 B2

(12) United States Patent
Hornung et al.

(10) Patent No.: US 9,921,588 B2
(45) Date of Patent: Mar. 20, 2018

(54) DETERMINATION OF FLUID COMPOSITION IN A MASS FLOW CONTROLLER

(71) Applicant: Sensirion AG, Stäfa (CH)

(72) Inventors: Mark Hornung, Stäfa (CH); Remo Fürst, Stäfa (CH); Thomas Huber, Stäfa (CH)

(73) Assignee: Sensirion AG, Stäfa (CH)

( * ) Notice: Subject to any disclaimer, the term of this patent is extended or adjusted under 35 U.S.C. 154(b) by 66 days.

(21) Appl. No.: 14/958,167

(22) Filed: Dec. 3, 2015

(65) Prior Publication Data
US 2016/0161951 A1    Jun. 9, 2016

(30) Foreign Application Priority Data
Dec. 4, 2014 (EP) .................................... 14196314

(51) Int. Cl.
*G05D 7/00* (2006.01)
*G01N 25/18* (2006.01)
(Continued)

(52) U.S. Cl.
CPC .............. *G05D 7/00* (2013.01); *G01F 1/6845* (2013.01); *G01F 1/692* (2013.01); *G01F 1/6965* (2013.01);
(Continued)

(58) Field of Classification Search
CPC ......... G05D 7/00; G01F 1/6845; G01F 1/692; G01F 1/6965; G01F 1/74; G01N 25/18; G01N 33/0027; Y10T 137/0324
See application file for complete search history.

(56) References Cited

U.S. PATENT DOCUMENTS 5,515,295 A * 5/1996 Wang .................... G01F 1/6845
                                                                702/113
5,980,102 A * 11/1999 Stulen ..................... G01N 25/18
                                                                374/138
(Continued)

FOREIGN PATENT DOCUMENTS

DE         101 29 300 A1    2/2002
EP         0 890 828 A1     1/1999
(Continued)

OTHER PUBLICATIONS

Sensirion, SFC4000 Ultra-Fast CMOSens® Mass Flow Controller for Gases, Product Summary, v.2.6, Jan. 2012 (16 pgs.)
(Continued)

*Primary Examiner* — Craig Schneider
*Assistant Examiner* — Kevin Barss
(74) *Attorney, Agent, or Firm* — Foley & Lardner LLP (57) ABSTRACT

A method for determining a fluid composition parameter, e.g., a fluid identifier, a mixing ratio or a parameter describing heat transfer properties, of an unknown fluid in a mass flow controller is disclosed. A control valve of the mass flow controller is set so as to establish a constant flow, preferably zero flow, through the mass flow controller. A heating element of the flow sensor is heated, and at least one temperature value is measured with temperature sensors arranged on both sides of the heater while the fluid contacts the flow sensor. First calibration data (LUT1) are retrieved. The first calibration data have, as input values, temperature values measured with the flow sensor at the previously established constant flow and have, as output values, values of the fluid composition parameter. The first calibration data are used to determine the fluid composition parameter from the measured temperature value.

22 Claims, 5 Drawing Sheets

(51) Int. Cl.
  *G01N 33/00*   (2006.01)
  *G01F 1/684*   (2006.01)
  *G01F 1/692*   (2006.01)
  *G01F 1/696*   (2006.01)
  *G01F 1/74*    (2006.01)

(52) U.S. Cl.
  CPC ............... *G01F 1/74* (2013.01); *G01N 25/18* (2013.01); *G01N 33/0027* (2013.01)

(56) References Cited

U.S. PATENT DOCUMENTS

| | | | |
|---|---|---|---|
| 6,550,324 B1 * | 4/2003 | Mayer | G01F 1/6986 |
| | | | 73/204.14 |
| 6,763,710 B2 * | 7/2004 | Mayer | G01F 1/6845 |
| | | | 73/204.11 |
| 7,188,519 B2 | 3/2007 | Hornung et al. | |
| 7,490,511 B2 * | 2/2009 | Mayer | G01F 1/6845 |
| | | | 73/204.15 |
| 7,644,613 B2 * | 1/2010 | Mayer | G01F 1/6845 |
| | | | 73/204.26 |
| 7,905,140 B2 * | 3/2011 | Kanne | B01L 3/502707 |
| | | | 73/204.26 |
| 8,011,240 B2 * | 9/2011 | von Waldkirch | G01F 1/6845 |
| | | | 219/201 |
| 8,408,050 B2 | 4/2013 | Mayer et al. | |

FOREIGN PATENT DOCUMENTS

| | | |
|---|---|---|
| EP | 2 175 246 A1 | 4/2010 |
| EP | 2 527 779 A2 | 11/2012 |
| WO | WO 01/18500 A1 | 3/2001 |
| WO | WO 01/98736 A1 | 12/2001 |
| WO | WO 2012/021999 A1 | 2/2012 |

OTHER PUBLICATIONS

Extended European Search Report dated May 27, 2015 in related European Appl. No. 14193614,0 (8 pgs.)

* cited by examiner

DETERMINATION OF FLUID COMPOSITION IN A MASS FLOW CONTROLLER

TECHNICAL FIELD

The present invention relates to a method for determining a fluid composition parameter of an unknown fluid in a mass flow controller, and to a mass flow controller and a computer program that are configured to carry out such a method. The fluid composition parameter can include, e.g., an identifier for the fluid, a mixing ratio, or any other parameter that characterizes the fluid, including parameters that characterize the heat transfer behavior of the fluid, such as the thermal conductivity.

PRIOR ART

WO 01/18500 discloses a device for measuring the mass flow of a fluid with a thermal mass flow sensor. The mass flow sensor comprises a heating element arranged between two temperature sensors, the temperature sensors being located upstream and downstream of the heating element, respectively. A temperature difference between the two temperature sensors is measured. If the heat transfer behavior of the fluid is known, the mass flow can be directly derived from the temperature difference. In order to determine a parameter that characterizes the heat transfer behavior of the fluid, the device comprises a second sensor, which is located in a region with no or only very little mass flow. The second sensor is structured similarly to the above-described flow sensor. A parameter that characterizes the heat transfer behavior of the fluid is measured with the second sensor. The parameter can be, e.g., the heat conductivity, the specific or volumetric heat capacity or the heat diffusivity. A disadvantage of this method is that it requires two sensors, and that it is necessary to create a region of no or very little mass flow.

In U.S. Pat. No. 7,188,519 and U.S. Pat. No. 8,408,050, both the mass flow and the thermal conductivity of a fluid are determined with only a single flow sensor. The flow sensor is structured as in the above-discussed document WO 01/18500. While the flow sensor is exposed to the fluid flow, two measured quantities are determined by means of the two temperature sensors, a first of which can be the difference between the temperatures, while the second can be one of the absolute temperatures or a (possibly weighted) sum of the temperatures. By comparing the two measured quantities, the mass flow and the thermal conductivity of the fluid can be determined. However, measurements with these methods are associated with relatively large measurement uncertainties, since two unknown variables are determined simultaneously.

A mass flow controller (MFC) is a device for measuring and controlling the flow of fluids (the term "fluid" including, in particular, gases). Mass flow controllers can be analog or digital. An analog mass flow controller is normally calibrated to control the flow of one specific fluid composition within a certain range of flow rates. A digital mass flow controller can be able to control more than one fluid composition by storing calibration data for different fluid compositions. In this case, it is important to know the composition of the fluid that is actually passed through the mass flow controller in order to be able to select the appropriate calibration data.

SUMMARY OF THE INVENTION

It is an object of the present invention to provide a method for determining a fluid composition parameter of an unknown fluid in a mass flow controller.

It is a further object of the present invention to provide a mass flow controller that is configured to carry out a determination of a fluid composition parameter of an unknown fluid.

It is another object to provide a computer program that, when carried out in a processor of a mass flow controller, carries out a determination of a fluid composition parameter of an unknown fluid.

In a first aspect, the present invention provides a method for determining a fluid composition parameter of an unknown fluid in a mass flow controller, the mass flow controller comprising a flow sensor and a control valve, the flow sensor comprising a heating element arranged between a first and a second temperature sensor, the method comprising:

(a) actuating the control valve to establish a constant flow through the mass flow controller;
(b) activating the heating element of the flow sensor and measuring at least one temperature value with the first and/or second temperature sensors of the flow sensor while the fluid contacts the flow sensor;
(c) retrieving first calibration data, the first calibration data having, as input values, temperature values measured with the thermal flow sensor at said constant flow and having, as output values, said fluid composition parameter; and
(d) using the first calibration data to determine said fluid composition parameter from the measured temperature value.

Preferably, the constant flow established in step (a) is zero, i.e. the control valve is closed completely. If the constant flow is different from zero, the constant flow may be established by setting the control valve to a predetermined valve opening, or by setting the valve to a valve opening that causes a predetermined temperature difference between the first and the second temperature sensors when step (b) is carried out.

The first calibration data can be provided in the form of a first lookup table. The calibration data can be stored locally in a memory of the mass flow controller, or they can be retrieved from a remote network location by any appropriate file transfer protocol.

The fluid composition parameter can include at least one of the following:
- a fluid identifier selected from a set of predetermined fluid identifiers;
- a concentration parameter indicative of a mixing ratio of a binary mixture of two fluids;
- a heat conductivity parameter indicative of a heat conductivity of the fluid;
- a heat capacity parameter indicative of a molar, specific or volumetric heat capacity of the fluid; and
- a heat diffusivity parameter indicative of a heat diffusivity of the fluid.

A key advantage of the present invention is that the determination of the fluid composition parameter is carried out at constant flow, i.e. under controlled conditions. An unknown mass flow is only determined thereafter, once the fluid composition parameter is known. This greatly improves accuracy over methods in which both fluid flow rate and fluid composition are unknown variables in the same measurement.

A single temperature value as measured by one of the temperature sensors can be employed for determining the fluid composition parameter; however, it is also conceivable to employ both temperature values or to employ one or more parameters derived from these temperature values, such as a (possibly weighted) sum of the temperature values.

The method can further comprise outputting the fluid composition parameter through a user interface, e.g., to an external application for further processing, or directly to the user via a display.

In a preferred embodiment, the method comprises:
(f) retrieving second calibration data, the second calibration data having, as input values, values of the fluid composition parameter and values of a temperature difference or temperature ratio between the first and second temperature sensors, and having, as output values, mass flow values; and
(f) operating the mass flow controller employing the second calibration data associated with the fluid composition parameter determined in step (d).

Step (f) can include any known control procedure for mass flow control. In particular, step (f) may comprise the following substeps:
(f1) activating the heating element of the flow sensor and measuring a temperature difference or temperature ratio between the first and second temperature sensors of the flow sensor while the fluid contacts the flow sensor;
(f2) using the second calibration data to determine a value of the mass flow from the measured temperature difference or temperature ratio and the fluid composition parameter determined in step (d);
(f3) deriving a valve signal from values of the mass flow determined in step (f2) and values of a desired mass flow value;
(f4) setting the control valve according to the valve signal; and
(f5) repeating steps (f1)-(f4).

The second calibration data can be provided in the form of a second lookup table. Like the first calibration data, also the second calibration data can be stored locally in a memory of the mass flow controller, or they can be retrieved from a remote network location.

In order to detect and alert the user to undesired states of the mass flow controller, the method may further comprise:
(g) determining whether the fluid composition parameter fulfills a warning condition;
(h) if the fluid composition parameter fulfills the warning condition, outputting a warning message and/or operating the mass flow controller in a safety mode.

The safety mode may, in particular, involve reducing the operating range of the control valve or completely closing the control valve.

The method of the present invention may be used to detect whether a fluid has been completely purged from the mass flow controller after a fluid exchange. To this end, the method may comprise;
passing a first fluid through the mass flow controller;
subsequently, passing a second fluid through the mass flow controller;
determining the fluid composition parameter by carrying out steps (a)-(d) of the method described above;
determining whether the fluid composition parameter indicates a presence of the second fluid in the mass flow controller;
if the fluid composition parameter indicates a presence of the second fluid in the mass flow controller, outputting a purge completion signal, the purge completion signal indicating that the first fluid has been purged from the mass flow controller.

Subsequently, normal mass flow control can be carried out, employing a fluid composition parameter for the second fluid.

In another aspect, the present invention provides a mass flow controller that is adapted to carry out any of the methods as described above. The mass flow controller comprises:
a conduit having an inlet and an outlet for a fluid;
a flow sensor arranged in the conduit, the flow sensor comprising a heating element arranged between a first and a second temperature sensor;
a control valve; and
a digital control circuit comprising a memory.

According to the invention, the digital control circuit is configured to carry out a method as described above, in particular, a method comprising:
(a) actuating the control valve to establish a constant flow through the mass flow controller;
(b) activating the heating element of the flow sensor and measuring at least one temperature value with the first and/or second temperature sensors of the flow sensor while the fluid contacts the flow sensor;
(c) retrieving first calibration data, the first calibration data having, as input values, temperature values measured with the thermal flow sensor at said constant flow and having, as output values, said fluid composition parameter; and
(d) using the first calibration data to determine said fluid composition parameter from the measured temperature value.

In particular, the memory of the digital control circuit may store the first calibration data, and the digital control circuit may be configured to retrieve the first calibration data from the memory.

The memory may further store the second calibration data described above, and the digital control circuit may be configured to retrieve the second calibration data from the memory.

In yet another aspect, the present invention provides a computer program comprising computer program code that, when carried out in a processor of a digital control circuit of a mass flow controller comprising a flow sensor and a control valve, the flow sensor comprising a heating element arranged between a first and a second temperature sensor, causes the digital control circuit to carry out any of the methods as described above, in particular, a method comprising:
(a) actuating the control valve to establish a constant flow through the mass flow controller;
(b) activating the heating element of the flow sensor and measuring at least one temperature value with the first and/or second temperature sensors of the flow sensor while the fluid contacts the flow sensor;
(c) retrieving first calibration data, the first calibration data having, as input values, temperature values measured with the thermal flow sensor at said constant flow and having, as output values, said fluid composition parameter; and
(d) using the first calibration data to determine said fluid composition parameter from the measured temperature value.

The computer program can be provided in source code, in machine-executable code, or in any intermediate form of code like object code. It can be provided as a computer program product on a computer-readable medium in tangible form, e.g., on a CD-ROM or on a Flash ROM memory element, or it can be made available in the form of a network-accessible medium for download from one or more remote servers through a network.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DESCRIPTION OF PREFERRED EMBODIMENTS

Figure 1:
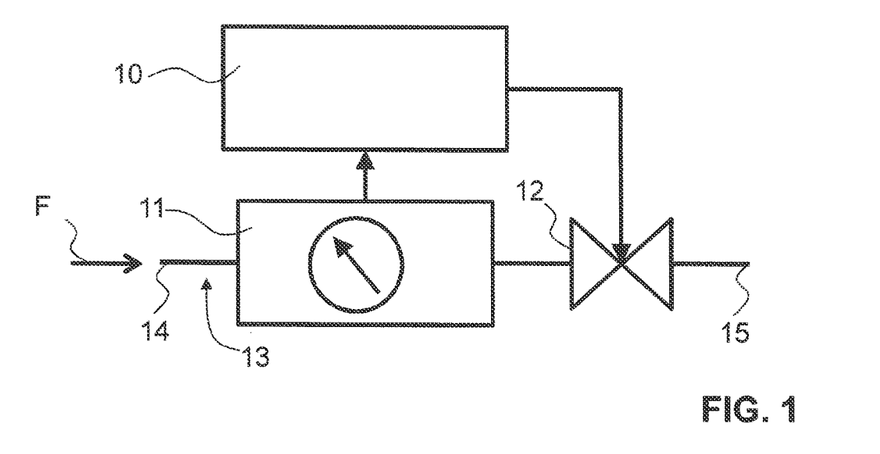
FIG. 1 is a schematic functional diagram of a mass flow controller.

FIG. 1 shows a schematic functional diagram of a mass flow controller. The mass flow controller comprises a control circuit 10, a mass flow sensor 11, and a proportional control valve 12. The mass flow sensor 11 is located upstream from the control valve 12 in a conduit 13 having an inlet 14 and an outlet 15. A fluid flow F passes through the conduit 13. The conduit 13 is illustrated only very schematically. It can take a variety of forms, as it is well known in the art. The mass flow sensor 11 can be arranged directly in the main flow within the conduit 13, or it can be arranged in a bypass portion of the conduit 13. Both configurations are well known in the art. For instance, the conduit 13 and the flow sensor 11 can be configured in the manner disclosed in WO 01/98736 A1, EP 2 527 779 A1 or WO 2012/021999 A1.

Figure 2:
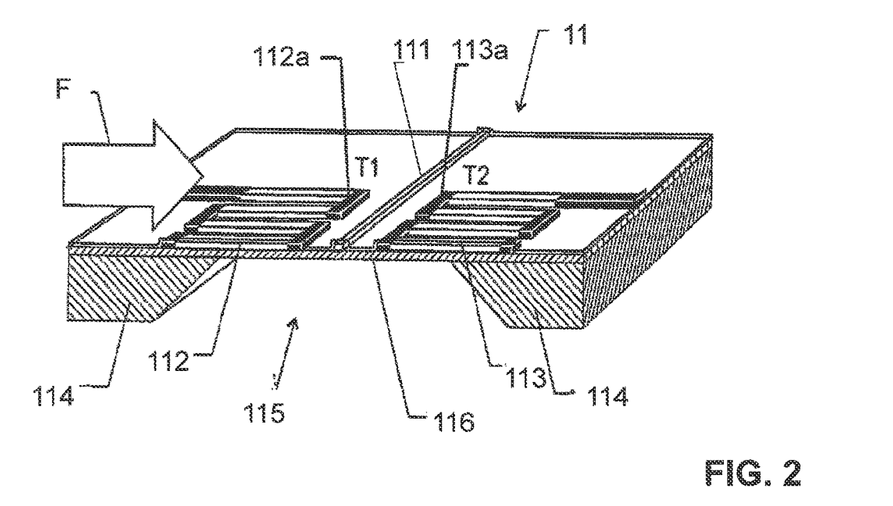
FIG. 2 is a schematic perspective sectional view of a flow sensor portion comprising the heater and the temperature sensors.
Figure 3:
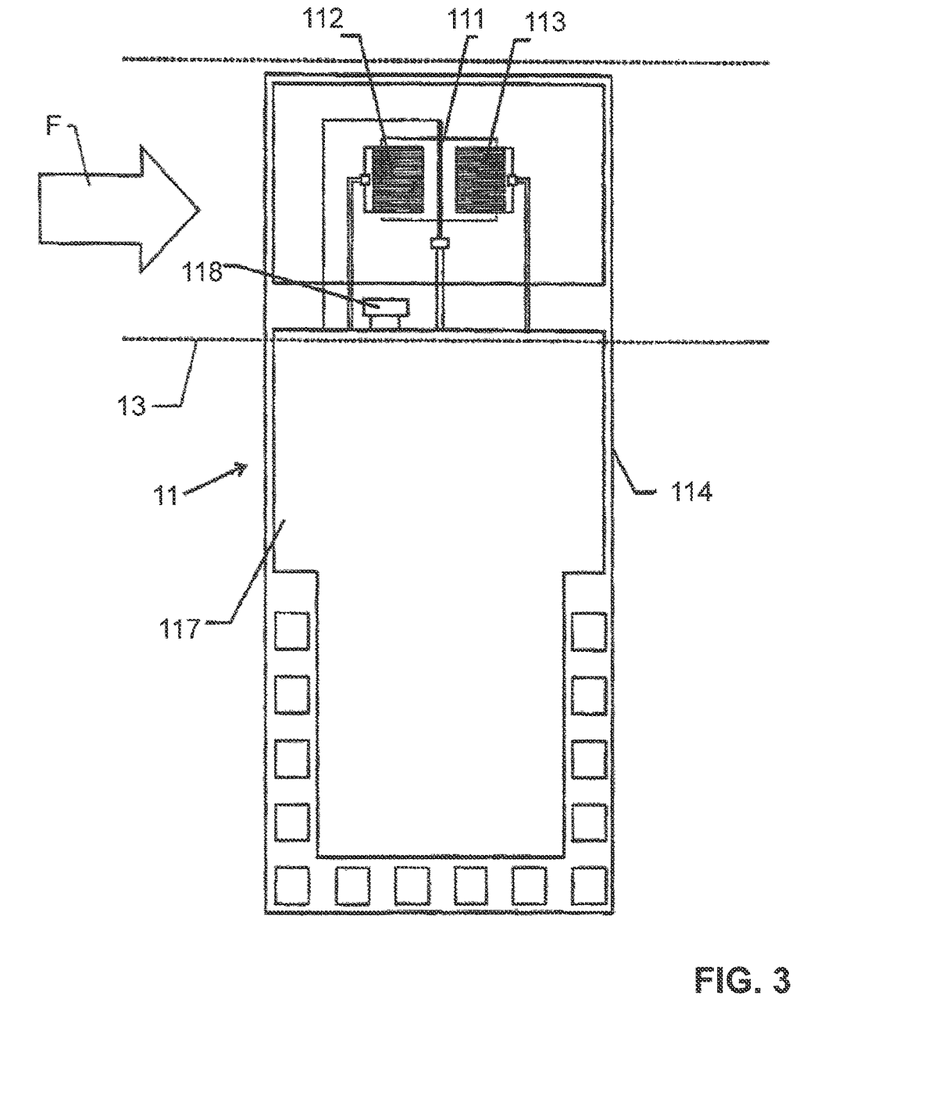
FIG. 3 is a schematic top view of the flow sensor in FIG. 2.

FIGS. 2 and 3 illustrate an example of a thermal mass flow sensor 11 as it is preferably employed in conjunction with the present invention. The mass flow sensor 11 comprises a resistive heater 111 arranged between a first temperature sensor 112 and a second temperature sensor 113. In the present embodiment, the temperature sensors 112, 113 are thermopiles; however, the invention can also be carried out with other types of temperature sensors, such as resistive temperature sensors. The flow sensor 11 further comprises a substrate 114, preferably a semiconductor substrate, in particular a silicon substrate. The heater 111, the temperature sensors 112, 113 as well as analog and digital circuitry 117 (e.g. analog amplifiers, an A/D-converter, and a digital signal processor) are integrated on a surface of the substrate 114. An opening or recess 115 in the substrate 114 has been manufactured e.g. by anisotropic etching; the recess 115 is spanned by a membrane 116. The temperature sensors 112, 113 as well as the heater 111 are arranged at least partially on the membrane 116 for good thermal insulation. A further temperature sensor 118 is arranged at a distance from the heater 111 in order to measure the temperature of a portion of the gas flow F that is unaffected by the heater 111.

At least the portion of the sensor 11 that comprises the heater 111 and the temperature sensors 112, 113 and 118 extends into the conduit 13, so as to be in thermal contact with the fluid flow F. The remaining part, including the analog and digital circuitry 117, can be arranged outside the conduit 13. This type of flow sensor is e.g. described in WO 01/98736 A1 and U.S. Pat. No. 7,188,519 B2, and the disclosure of these documents is incorporated herein by reference in its entirety for teaching the setup of a flow sensor.

The flow sensor 11 can be operated in at least two different modes. A first mode will in the following be called a "differential" mode. This mode is employed to measure the fluid flow. A second mode will be called an "absolute" mode. This mode serves for determining a fluid composition parameter. Both modes will now be described in more detail.

First, "differential" mode is described. In this mode, a fluid flow F is passed over first temperature sensor 112, then heater 111 and finally second temperature sensor 113. Heater 111 is heated by an electric current, advantageously to a temperature that lies at a fixed offset above the temperature of substrate 114. Thermal conductance through membrane 116 as well as through the fluid leads to a temperature increase at the inner contacts 112a, 113a of the temperature sensors 112, 113, while the outer contacts remain at the bulk temperature of substrate 114. In the presence of a non-zero flow, the temperature distribution is asymmetric, and the temperature T1 measured by first temperature sensor 112 will generally be lower than the temperature T2 measured by second temperature sensor 113.

Figure 4:
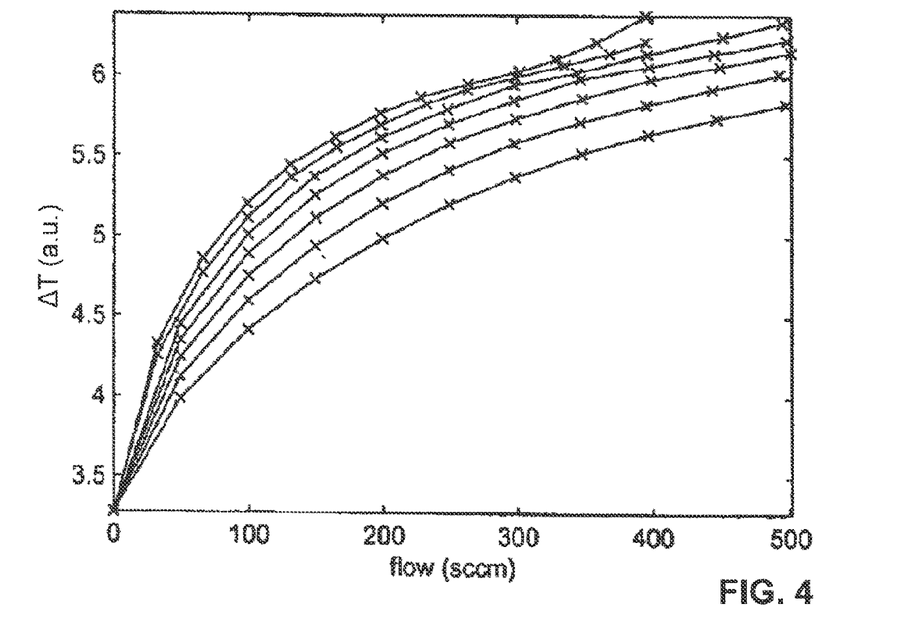
FIG. 4 is a diagram illustrating the dependence between a temperature difference ΔT as measured by a thermal mass flow sensor and the flow rate of the fluid for a plurality of different fluid compositions.

The temperature difference ΔT=T2−T1 between the second and the first temperatures T2 and T1 (or, equivalently, the ratio of these temperatures) depends, inter alia, on the mass flow and on the heat transfer properties of the fluid, in particular, on its heat conductivity and heat capacity. The temperature difference can be used to quantify the mass flow if the identity of the fluid is known. This is illustrated in FIG. 4, which shows the dependency between flow (in standard cubic centimeters per minute) and temperature difference ΔT (in arbitrary units; a value of 3.25 corresponding to a temperature difference of 0° C.) for a variety of different fluid compositions. In the specific example shown here, the fluid was a mixture of air and n-butane ($C_4H_{10}$). The bottommost curve corresponds to a measurement where the content of n-butane was 0%, the second curve from the bottom corresponds to a fluid with a n-butane content of 10%, the third curve to a fluid with a n-butane content of 20%, etc., with the topmost curve corresponding to a fluid with a n-butane content of 60%. If the fluid composition is known, the corresponding curve provides a direct relationship between the measured temperature difference and the mass flow. Such relationships can readily be measured for a plurality of reference compositions and stored as calibration data in a lookup table.

Next, "absolute" mode will be described. In this mode, the sensor is generally operated in the same manner as in "differential" mode. However, instead of determining a temperature difference between the first and second temperatures, the absolute temperatures T1 and T2 are measured, or a single temperature value TS is derived from T1 and T2. This single temperature value TS can be, e.g., one of the temperatures T1 or T2 or a (possibly weighted) sum of both. In some embodiments, the single temperature value TS can, e.g., be expressed as TS=k1*[k2*T1+(1−k2)*T2], where k1 is an arbitrary constant and k2 is a real number between 0 and 1.

Again, the temperatures T1, T2 or the single temperature value TS depend both on the mass flow rate and on the heat transfer properties, in particular on the heat conductivity, of the fluid. If the mass flow rate is known, the heat conductivity can be derived from the temperatures T1 and T2 or from the single temperature value TS. If it is further known what kinds of fluids can in principle be present in the conduit, e.g., if it is known that the fluid is always selected from only a few possible fluid compositions, or if it is known that the fluid is a binary mixture of two components, it is furthermore possible to identify the composition of the fluid in the conduit, because the heat conductivity generally depends on the composition. In more general terms, a fluid composition parameter can be determined from the measurement in "absolute" mode at known flow conditions. The relationship between the temperatures in "absolute" mode and the fluid composition parameter at particular flow conditions can be stored as calibration data in another lookup table.

Figure 5:
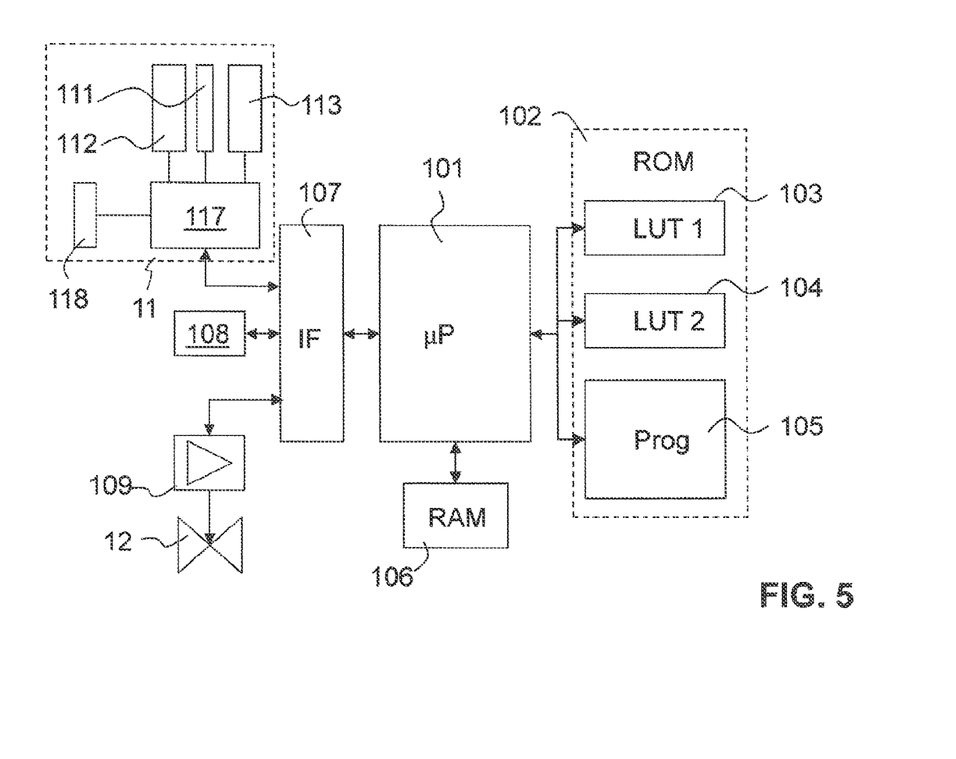
FIG. 5 is a simplified block diagram of a digital control circuit for a mass flow controller.

A simplified and highly schematic block diagram of a digital control circuit 10 for a mass flow controller is shown in FIG. 5. The control circuit comprises a processor (CPU, µP) 101, a non-volatile (e.g., Flash ROM) memory 102, and a volatile (RAM) memory 106. The processor 101 communicates with the memory modules 102, 106. The non-volatile memory 102 stores, inter alia, plural sets of calibration data 103, 104 in the form of lookup tables LUT1, LUT2, as well as a machine-executable program 105 for execution in the processor 101. Lookup table LUT1 includes calibration data for measurements in "absolute" mode, while lookup table LUT2 includes calibration data for measurements in "differential" mode for a plurality of compositional parameters.

Via a data interface 107, the processor 101 communicates with various peripherals, including the sensor 11, a user interface 108 (which may include, e.g., at least one of a network interface for interfacing with an external input/output device, a dedicated input device such as a keyboard and/or mouse, and a dedicated output device, such as an LCD screen), and a driver 109 for control valve 12.

Figure 6:
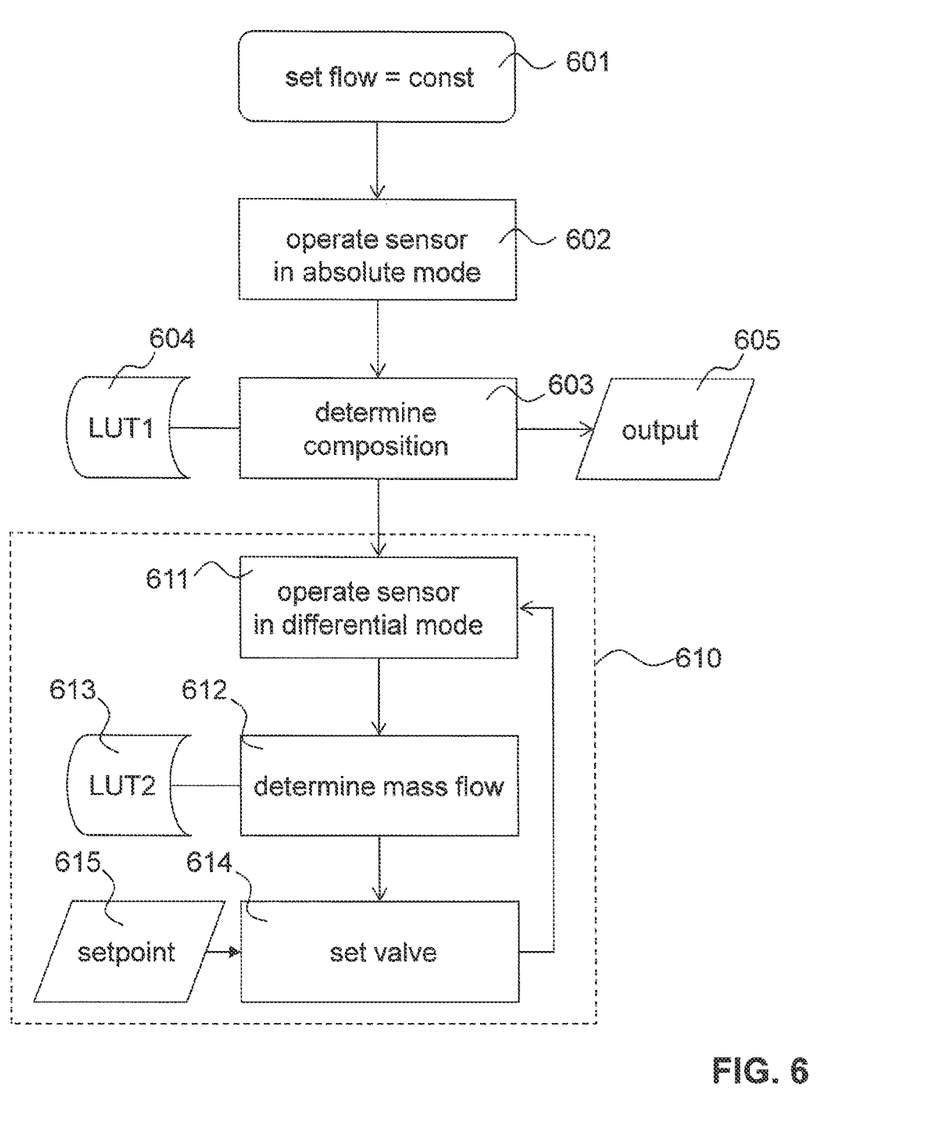
FIG. 6 shows a flow diagram of a method according to a first embodiment of the present invention.

FIG. 6 illustrates how the mass flow controller can be operated for determining an unknown fluid composition. In step 601, the processor 101 sets the control valve to a predetermined opening value so as to establish well-defined, constant flow conditions through the mass flow controller. Preferably the flow established in this manner is zero, i.e. the control valve is completely closed.

Next, the processor 101 commands the sensor 11 to carry out a measurement in "absolute" mode (step 602). From this measurement, a fluid composition parameter is determined (step 603) with the aid of lookup table LUT1 (box 604).

The calibration data in lookup table LUT1 provide a 1:1 relationship between values of the compositional parameter and measurement results in "absolute" mode at the flow rate established in step 601. For instance, if it is known that the fluid in conduit 13 is a binary mixture of two gases, lookup table LUT1 may store a single temperature value TS for each of a plurality of mixing ratios between the two gases. In another example, if it is known that the fluid in the conduit is one of methane, ethane, propane and butane, lookup table LUT1 may store a single temperature value TS or a range of single temperature values for each of these four gases. Processor 101 queries lookup table LUT1 (box 604) to determine a fluid composition parameter from the single temperature value TS (step 603).

The processor now outputs the fluid composition parameter and optionally additional associated data through user interface 108 (box 605). For instance, the processor may output the temperatures T1 and T2, the single temperature value TS derived from these temperatures, the heat conductivity determined from these values, and/or a fluid identifier (in the case of a selection from a plurality of possible gases) or a mixing ratio (in the case of a binary mixture).

Subsequently, normal mass flow control is carried out, using the fluid composition parameter that has been determined in this manner (control loop 610). To this end, lookup table LUT2 is employed. The calibration data in lookup table LUT2 has two input variables, namely, the temperature difference determined in "differential" mode and the fluid composition parameter, and one output variable, namely, the mass flow. In a simple implementation, lookup table LUT2 may comprise a two-dimensional array having rows and columns, each column corresponding to a certain value of the fluid composition parameter, and each row corresponding to a certain value of the temperature difference, the entries in the array corresponding to the associated mass flow values. Other, more complex implementations are conceivable. For instance, the lookup table LUT2 may comprise a set of coefficients describing a functional relationship between temperature difference values and mass flow values, e.g., the coefficients of a Taylor expansion, for a plurality of fluid composition parameters.

In the simple implementation described above, the processor would simply select that column from the lookup table LUT2 that most closely belongs to the value of the fluid composition parameter that was determined in step 603 (step 606), or would interpolate between the two closest columns. In the case of a binary mixture, the processor would, e.g., select that column in lookup table LUT2 that belongs most closely to the mixing ratio determined in step 603. In the case of a selection from a limited number of known compositions, the processor would select that column in lookup table LUT2 that corresponds to the composition determined in step 603. It is then possible to determine a mass flow value for each measured temperature difference by interpolation between the values in that single column.

For carrying out normal mass flow control, the microprocessor causes the mass flow sensor to operate in the "differential" mode to obtain a temperature difference (step. 611); it uses the calibration data in the lookup table LUT2 (box 613) to determine a value of the actual mass flow from the temperature difference and the fluid composition parameter determined in step 603 (step 612); it receives a desired mass flow value (setpoint) from the user interface (box 615), calculates a valve setting based on the actual mass flow and the desired mass flow according to well-known control procedures like PID control, and sets the valve accordingly (614) before it repeats step 611.

If the composition determined in step 603 is incompatible with the expected composition or range of compositions, the processor may output a warning message through user interface 108. It may further enter a safety mode, in which, e.g., the opening range of valve 12 may be restricted, or in which valve 12 is completely closed. For instance, in the example of a mixture of air and n-butane discussed above, if the second lookup table LUT2 contained only the data shown in FIG. 4, and if the fluid composition parameter determined in step 603 indicated an n-butane content above 60%, the warning message would be outputted, and safety mode would be entered, because lookup table LUT2 would lack data for such a mixing ratio.

Figure 7:
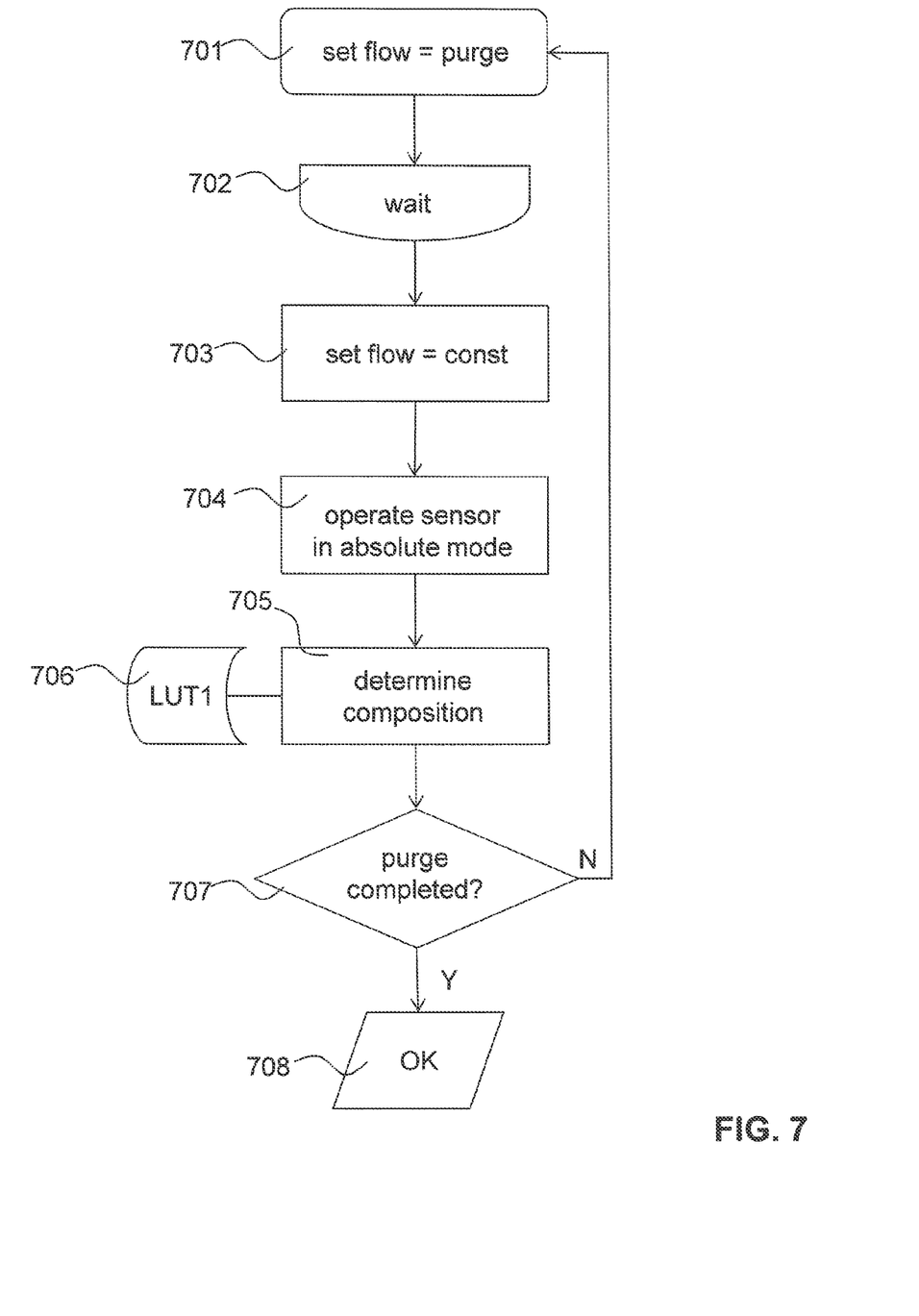
FIG. 7 shows a flow diagram of a method according to a second embodiment of the present invention.

FIG. 7 illustrates an embodiment in which the present invention is employed to determine whether the mass flow controller has been correctly purged after a change in fluid composition. In step 701, the processor opens control valve 12 to establish a relatively large flow, so as to purge the system of the fluid that had previously been used. After a waiting time 702, the processor causes the control valve to assume a predetermined setting, so as to establish a constant flow in the mass flow controller (preferably zero flow). The processor now operates the sensor in "absolute" mode (step 704) and uses lookup table LUT1 (box 706) to determine a fluid composition parameter. If the fluid composition parameter indicates that the purge with the new fluid has not yet been completed, steps 701-705 are repeated (decision 707); otherwise the purge is considered to be complete, and the result is outputted through the user interface. Subsequently, normal mass flow control can be carried out, as in the first embodiment.

All or part of control circuit 10 can be integrated on semiconductor substrate 114; however, part or all of this circuit may also be implemented as external circuitry. In particular, all or part of the control circuit may be implemented as a general-purpose computer that executes software that causes the processor of the computer to carry out the above-described steps. Consequently, the presently described method can be embodied in a computer program for execution on a general-purpose computer or on a processor of a dedicated control circuit.

While there are shown and described presently preferred embodiments of the invention, it is to be understood that the invention is not limited thereto but may be otherwise variously embodied and practiced within the scope of the following claims.

The invention claimed is:

1. A method for determining a fluid composition parameter of an unknown fluid in a mass flow controller, the mass flow controller comprising a flow sensor and a control valve, the flow sensor comprising a heating element arranged between a first and a second temperature sensor, the method comprising:
   (a) actuating the control valve to establish a constant flow through the mass flow controller;
   (b) activating the heating element of the flow sensor and measuring at least one temperature value with the first and/or second temperature sensors of the flow sensor while the fluid contacts the flow sensor;
   (c) retrieving first calibration data, the first calibration data having, as input values, temperature values measured with the flow sensor at said constant flow and having, as output values, values of said fluid composition parameter;
   (d) using said first calibration data to determine said fluid composition parameter from the measured temperature value;
   (f) retrieving second calibration data, the second calibration data having, as input values, values of the fluid composition parameter and values of a temperature difference or temperature ratio between the first and second temperature sensors, and having, as output values, mass flow values; and
   (f') operating the mass flow controller employing the second calibration data associated with the fluid composition parameter determined in step (d),
   wherein step (f') comprises the following substeps:
      (f1) activating the heating element of the flow sensor and measuring a temperature difference or temperature ratio between the first and second temperature sensors of the flow sensor while the fluid contacts the flow sensor;
      (f2) using the second calibration data to determine a value of the mass flow from the measured temperature difference or temperature ratio and the fluid composition parameter determined in step (d);
      (f3) deriving a valve signal from values of the mass flow determined in step (f2) and values of a desired mass flow value;
      (f4) setting the control valve according to the valve signal; and
      (f5) repeating steps (f1)-(f4).

2. The method of claim 1, wherein the first calibration data include a first lookup table.

3. The method of claim 1, wherein the constant flow is zero.

4. The method of claim 1, wherein the fluid composition parameter includes at least one of the following:
   a fluid identifier selected from a set of predetermined fluid identifiers;
   a concentration parameter indicative of a mixing ratio of a binary mixture of two fluids;
   a heat conductivity parameter indicative of a heat conductivity of the fluid;
   a heat capacity parameter indicative of a molar, specific or volumetric heat capacity of the fluid; and
   a heat diffusivity parameter indicative of a heat diffusivity of the fluid.

5. The method of claim 1, further comprising:
   (e) outputting the fluid composition parameter.

6. The method of claim 1, further comprising:
   (g) determining whether the fluid composition parameter fulfills a warning condition;
   (h) if the fluid composition parameter fulfills the warning condition, outputting a warning message and/or operating the mass flow controller in a safety mode.

7. A mass flow controller comprising:
   a conduit having an inlet and an outlet for a fluid;
   a flow sensor arranged in the conduit, the flow sensor comprising a heating element arranged between a first and a second temperature sensor;
   a control valve; and
   a digital control circuit comprising a memory, the digital control circuit being configured to carry out a method comprising:
      (a) actuating the control valve to establish a constant flow through the mass flow controller;
      (b) activating the heating element of the flow sensor and measuring at least one temperature value with the first and/or second temperature sensors of the flow sensor while the fluid contacts the flow sensor;
      (c) retrieving first calibration data, the first calibration data having, as input values, temperature values measured with the flow sensor at said constant flow and having, as output values, values of said fluid composition parameter;
      (d) using said first calibration data to determine said fluid composition parameter from the measured temperature values;
      (f) retrieving second calibration data, the second calibration data having, as input values, values of the fluid composition parameter and values of a temperature difference or temperature ratio between the first and second temperature sensors, and having, as output values, mass flow values; and (f') operating the mass flow controller employing the second calibration data associated with the fluid composition parameter determined in step (d),
wherein step (f) comprises the following substeps:
(f1) activating the heating element of the flow sensor and measuring a temperature difference or temperature ratio between the first and second temperature sensors of the flow sensor while the fluid contacts the flow sensor;
(f2) using the second calibration data to determine a value of the mass flow from the measured temperature difference or temperature ratio and the fluid composition parameter determined in step (d);
(f3) deriving a valve signal from values of the mass flow determined in step (f2) and values of a desired mass flow value;
(f4) setting the control valve according to the valve signal; and
(f5) repeating steps (f1)-(f4).

8. The mass flow controller of claim 7, wherein the memory stores the first calibration data, and wherein the digital control circuit is configured to retrieve the first calibration data from the memory.

9. The mass flow controller of claim 7, wherein the memory stores the second calibration data, and wherein the digital control circuit is configured to retrieve the second calibration data from the memory.

10. The mass flow controller of claim 7, wherein the first calibration data include a first lookup table.

11. The mass flow controller of claim 7, wherein the constant flow is zero.

12. The mass flow controller of claim 7, wherein the fluid composition parameter includes at least one of the following:
a fluid identifier selected from a set of predetermined fluid identifiers;
a concentration parameter indicative of a mixing ratio of a binary mixture of two fluids;
a heat conductivity parameter indicative of a heat conductivity of the fluid;
a heat capacity parameter indicative of a molar, specific or volumetric heat capacity of the fluid; and
a heat diffusivity parameter indicative of a heat diffusivity of the fluid.

13. The mass flow controller of claim 7, wherein the digital control circuit is configured to output the fluid composition parameter.

14. The mass flow controller of claim 7, wherein the digital control circuit is configured to carry out the following steps:
(g) determining whether the fluid composition parameter fulfills a warning condition;
(h) if the fluid composition parameter fulfills the warning condition, outputting a warning message and/or operating the mass flow controller in a safety mode.

15. A computer-readable medium in tangible form comprising a computer program comprising computer program code that, when carried out in a digital control circuit of a mass flow controller comprising a flow sensor and a control valve, the flow sensor comprising a heating element arranged between a first and a second temperature sensor, causes the digital control circuit to carry out a method comprising:
(a) actuating the control valve to establish a constant flow through the mass flow controller;
(b) activating the heating element of the flow sensor and measuring at least one temperature value with the first and/or second temperature sensors of the flow sensor while the fluid contacts the flow sensor;
(c) retrieving first calibration data, the first calibration data having, as input values, temperature values measured with the flow sensor at said constant flow and having, as output values, values of said fluid composition parameter;
(d) using said first calibration data to determine said fluid composition parameter from the measured temperature values;
(f) retrieving second calibration data, the second calibration data having, as input values, values of the fluid composition parameter and values of a temperature difference or temperature ratio between the first and second temperature sensors, and having, as output values, mass flow values; and
(f') operating the mass flow controller employing the second calibration data associated with the fluid composition parameter determined in step (d),
wherein step (f') comprises the following substeps:
(f1) activating the heating element of the flow sensor and measuring a temperature difference or temperature ratio between the first and second temperature sensors of the flow sensor while the fluid contacts the flow sensor;
(f2) using the second calibration data to determine a value of the mass flow from the measured temperature difference or temperature ratio and the fluid composition parameter determined in step (d);
(f3) deriving a valve signal from values of the mass flow determined in step (f2) and values of a desired mass flow value;
(f4) setting the control valve according to the valve signal; and
(f5) repeating steps (f1)-(f4).

16. A method for determining a fluid composition parameter of an unknown fluid in a mass flow controller, the mass flow controller comprising a flow sensor and a control valve, the flow sensor comprising a heating element arranged between a first and a second temperature sensor, the method comprising:
passing a first fluid through the mass flow controller;
passing a second fluid through the mass flow controller;
determining the fluid composition parameter by carrying out steps that include steps (a)-(d):
(a) actuating the control valve to establish a constant flow through the mass flow controller;
(b) activating the heating element of the flow sensor and measuring at least one temperature value with the first and/or second temperature sensors of the flow sensor while the fluid contacts the flow sensor;
(c) retrieving first calibration data, the first calibration data having, as input values, temperature values measured with the flow sensor at said constant flow and having, as output values, values of said fluid composition parameter;
(d) using said first calibration data to determine said fluid composition parameter from the measured temperature value; and
determining whether the fluid composition parameter indicates a presence of the second fluid in the mass flow controller;
if the fluid composition parameter indicates a presence of the second fluid in the mass flow controller, outputting a purge completion signal, the purge completion signal indicating that the first fluid has been purged from the mass flow controller.

17. The method of claim 16, wherein the constant flow is zero.

18. The method of claim 16, wherein the fluid composition parameter includes at least one of the following:
   a fluid identifier selected from a set of predetermined fluid identifiers;
   a concentration parameter indicative of a mixing ratio of a binary mixture of two fluids;
   a heat conductivity parameter indicative of a heat conductivity of the fluid;
   a heat capacity parameter indicative of a molar, specific or volumetric heat capacity of the fluid; and
   a heat diffusivity parameter indicative of a heat diffusivity of the fluid.

19. A mass flow controller comprising:
   a conduit having an inlet and an outlet for a fluid;
   a flow sensor arranged in the conduit, the flow sensor comprising a heating element arranged between a first and a second temperature sensor;
   a control valve; and
   a digital control circuit comprising a memory, the digital control circuit being configured to carry out a method comprising:
      passing a first fluid through the mass flow controller;
      passing a second fluid through the mass flow controller;
      determining the fluid composition parameter by carrying out steps that include steps (a)-(d):
         (a) actuating the control valve to establish a constant flow through the mass flow controller;
         (b) activating the heating element of the flow sensor and measuring at least one temperature value with the first and/or second temperature sensors of the flow sensor while the fluid contacts the flow sensor;
         (c) retrieving first calibration data, the first calibration data having, as input values, temperature values measured with the flow sensor at said constant flow and having, as output values, values of said fluid composition parameter;
         (d) using said first calibration data to determine said fluid composition parameter from the measured temperature values; and
      determining whether the fluid composition parameter indicates a presence of the second fluid in the mass flow controller;
      if the fluid composition parameter indicates a presence of the second fluid in the mass flow controller, outputting a purge completion signal, the purge completion signal indicating that the first fluid has been purged from the mass flow controller.

20. The mass flow controller of claim 19, wherein the constant flow is zero.

21. The mass flow controller of claim 19, wherein the fluid composition parameter includes at least one of the following:
   a fluid identifier selected from a set of predetermined fluid identifiers;
   a concentration parameter indicative of a mixing ratio of a binary mixture of two fluids;
   a heat conductivity parameter indicative of a heat conductivity of the fluid;
   a heat capacity parameter indicative of a molar, specific or volumetric heat capacity of the fluid; and
   a heat diffusivity parameter indicative of a heat diffusivity of the fluid.

22. A computer-readable medium in tangible form comprising a computer program comprising computer program code that, when carried out in a digital control circuit of a mass flow controller comprising a flow sensor and a control valve, the flow sensor comprising a heating element arranged between a first and a second temperature sensor, causes the digital control circuit to carry out a method comprising:
   passing a first fluid through the mass flow controller;
   passing a second fluid through the mass flow controller;
   determining the fluid composition parameter by carrying out steps that include (a)-(d):
      (a) actuating the control valve to establish a constant flow through the mass flow controller;
      (b) activating the heating element of the flow sensor and measuring at least one temperature value with the first and/or second temperature sensors of the flow sensor while the fluid contacts the flow sensor;
      (c) retrieving first calibration data, the first calibration data having, as input values, temperature values measured with the flow sensor at said constant flow and having, as output values, values of said fluid composition parameter;
      (d) using said first calibration data to determine said fluid composition parameter from the measured temperature values; and
   determining whether the fluid composition parameter indicates a presence of the second fluid in the mass flow controller;
   if the fluid composition parameter indicates a presence of the second fluid in the mass flow controller, outputting a purge completion signal, the purge completion signal indicating that the first fluid has been purged from the mass flow controller.

* * * * *